(12) United States Patent
Chen et al.

(10) Patent No.: US 6,592,618 B2
(45) Date of Patent: Jul. 15, 2003

(54) IN VITRO MODIFICATION OF CARDIAC VALVULAR XENOGRAFTS

(75) Inventors: Raymond H. Chen, Boston, MA (US); David H. Adams, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/793,400

(22) Filed: Feb. 27, 2001

(65) Prior Publication Data

US 2001/0032015 A1 Oct. 18, 2001

Related U.S. Application Data

(60) Provisional application No. 60/185,747, filed on Feb. 29, 2000, now abandoned.

(51) Int. Cl.$^7$ ................................................. A61F 1/22
(52) U.S. Cl. ........................ 623/2.13; 600/36; 8/94.11; 623/915; 623/916; 623/917; 623/918
(58) Field of Search ........................ 623/2.13, 915–918; 600/36; 8/94.11

(56) References Cited

U.S. PATENT DOCUMENTS

| | | | |
|---|---|---|---|
| 3,983,581 A | 10/1976 | Angell et al. .................... 3/1.5 |
| 4,035,849 A | 7/1977 | Angell et al. .................... 3/1.5 |
| 5,861,028 A | 1/1999 | Angell ............................ 623/2 |
| 5,882,328 A * | 3/1999 | Levy et al. ..................... 604/20 |
| 6,214,407 B1 | 4/2001 | Laube et al. ................. 427/2.24 |
| 6,383,732 B1 * | 5/2002 | Stone ........................... 435/1.1 |

FOREIGN PATENT DOCUMENTS

| | | | |
|---|---|---|---|
| DE | 198 34 396 | 2/2000 | ........... A61L/27/00 |
| EP | 0 994 185 | 4/2000 | ............ C12N/5/08 |

OTHER PUBLICATIONS

Chen, et al., "Decreased Porcine Valve Antigenicity With In Vitro Culture," *Ann. of Thorac. Surg.*71:S393–S395 (2001).
Ohkado, et al., "Problems in Preservation of Allogeneic Heart Valves and Vessels," *Transplantation Proceedings* 31:2047–2048 (1999).
Abstract for All above.

* cited by examiner

*Primary Examiner*—David H. Willse
*Assistant Examiner*—Javier S. Blanco
(74) *Attorney, Agent, or Firm*—Michael A. Sanzo; Fitch, Even, Tabin & Flannery

(57) ABSTRACT

The present invention is directed to methods for obtaining heart valves from a donor animal that have a reduced tendency to cause inflammation when implanted into a human patient. The valves produced by this method should be less likely to undergo post-surgical degeneration.

21 Claims, No Drawings

IN VITRO MODIFICATION OF CARDIAC VALVULAR XENOGRAFTS

CROSS REFERENCE TO RELATED APPLICATIONS

The present application claims the benefit of U.S. provisional application No. 60/185,747, filed on Feb. 29, 2000 (now abandoned).

STATEMENT OF GOVERNMENT SUPPORT

The work leading to this invention was supported by one or more grants from the U.S. Government. The U.S. Government therefore has certain rights in the invention.

FIELD OF THE INVENTION

The present invention is directed to improved methods for preserving heart valves that have been removed from donor animals for transplantation into humans. The method involves treating the valves in a manner that reduces their expression of antigens causing inflammation after transplantation.

BACKGROUND OF THE INVENTION

Diseased heart valves maybe replaced with either mechanical or natural tissue prostheses. In the latter case, porcine valves are often used because of their similarity to valves in humans. The prior art teaches methods for removing heart valves from a pig, treating them with chemical solutions to aid in their preservation and then implanting them into a patient (U.S. Pat. Nos. 3,983,581; 4,035,849; and 5,861,028). Unfortunately, transplanted valves sometimes undergo relatively rapid degeneration and may need to be replaced. Methods for improving the biological performance of these valves would represent a clear advance in the treatment of cardiac patients.

SUMMARY OF THE INVENTION

The present invention is based upon the discovery that porcine cardiac valvular tissue continuously expresses antigens (e.g., major histocompatibility complex, "MHC," class II antigens), that cause inflammation upon implantation into a human host. Inflammation is believed to contribute to a decrease in the functional half-life of the xenografts. Therefore, a method has been developed in which valves are cultured in vitro (preferably in the presence of a biologically active substance modifying their immunological profile) prior to freezing or chemical preservation. In particular, it has been found that primate serum causes a decreased expression of MHC class II antigens in porcine valves. Thus, a valve is produced with a reduced tendency to undergo post-surgical deterioration.

In its first aspect, the invention is directed to a method of preparing a heart valve for transplantation by removing it from a donor animal; culturing it in vitro for a period of time sufficient to reduce antigens that cause inflammation after transplantation; and then preserving the valve by freezing or chemical treatment. Alternatively, the cultured valves may be implanted directly into a patient. It has been found that porcine valves cultured for 48 hours in the presence of primate serum (preferably baboon serum) show an essentially complete loss of MHCII antigens. It is expected that serum from other species distinct from the donor animal may also be used. In addition, the invention encompasses the heart valves prepared by these methods.

In a second aspect, the invention is directed to a heart valve obtained from a donor animal for transplantation into a human. These valves express less than 10% of the MHCII antigens normally found in the valve prior to, or immediately after, removal from the donor animal. Preferably, the donor is a pig and the level of MHCII antigens is reduced to less than 1%.

Finally, the invention is directed to the improvement in heart valve transplantation characterized by the in vitro culturing of valves after removal from a donor animal. Again, the objective of culturing is to reduce inflammation-causing antigens as much as possible. As discussed above, the incubation should generally be performed in the presence of an agent (e.g., primate serum) that aids in reducing antigen levels.

DETAILED DESCRIPTION OF THE INVENTION

Natural tissue heart valves for surgical implantation are typically obtained from porcine donors and must be preserved until surgery can be performed on an appropriate recipient. Although methods have been developed for surgically removing valves from animals and preserving them either by freezing or by treatment with chemicals, improved methods are needed to avoid the degeneration of valves post-implantation.

It has been found that valves derived from pigs express antigens that lead to inflammation upon implantation into humans. If, after removal from donor animals, the valves are incubated in vitro, the MHCII class of inflammatory antigens rapidly decreases so that, by 48 hours, such antigens are essentially absent. Incubations should generally be carried out in the presence of serum derived from a species other than the donor animal (e.g., primate serum) and should preferably be terminated in less than 5 days. Typically serum should comprise between 5% and 20% by volume of the growth medium.

Any of the standard methods for obtaining, culturing and preserving valves known in the art are compatible with the invention as is any type of growth medium provided that it contains serum as discussed above. Similarly, the actual implantation may be accomplished using standard surgical procedures. The valves produced by the methods disclosed herein should exhibit less inflammation in patients and have a substantially increased functional life.

EXAMPLES

Porcine valvular prostheses may stimulate inflammation after implantation with resultant accelerated structural degeneration. The present example investigates the expression of porcine MHC class II molecules on valve leaflets and methods of decreasing valve antigenicity by means of in vitro culture.

A. Materials and Methods

Aortic and pulmonary valves were dissected from domestic pigs under sterile conditions and cultured in vitro with either porcine or baboon serum for 5 days. Valves were harvested daily and fixed in Camoy's solution. Microtome sections of valves were examined by H&E, and by immunohistochemistry for porcine MHC class II proteins and an endothelial marker, alpha-N-acetylgalactosaminyl glycoprotein (alpha-GalNac).

B. Results

Porcine aortic and pulmonary valves constitutively express alpha-GalNac proteins and porcine MHC class II antigens. Porcine valves continue to express both alpha-GalNac and MHC class II proteins after 48 hours of culture in porcine serum. After 48 hours culture in baboon serum, however, MHC class II antigens become undetectable on valvular leaflets, although alpha-GalNac molecules are still detected. Neither alpha-GalNac nor MHC class II antigens could be detected after a 5-day culture with either serum.

C. Conclusions

Porcine valves can be cultured for 2 days in vitro and still maintain viable valvular endothelial cells. Porcine valves cultured with primate serum decreased MHC class II antigen expression. In vitro culture prior to glutaraldehyde fixation should decrease inflammation associated with valve implantation.

What is claimed is:

1. A heart valve obtained from a donor animal for transplantation into a human, wherein said heart valve expresses less than 10% of the MHC class II antigens normally found in said valve immediately after removal from said donor animal.

2. The heart valve of claim 1, wherein said valve expresses less than 1% of the MHC class II antigens normally found in said valve immediately after removal from said donor animal.

3. The heart valve of either claim 1 or claim 2, wherein said donor animal is a pig.

4. A method of preparing a heart valve for transplantation into a patient, comprising:
   (a) removing said heart valve from a donor animal;
   (b) culturing said heart valve in vitro in the presence of primate serum for a period of time sufficient to reduce antigens inducing inflammation upon transplantation; and
   (c) either:
      (I) implanting the cultured heart valve of step (b) into said patient; or
      (ii) preserving said heart valve by freezing or chemical treatment.

5. The method of claim 4, wherein said donor animal is a pig.

6. The method of claim 4, wherein said heart valve is cultured in growth medium containing said primate serum, and said primate serum constitutes between 5% and 20% by volume of the growth medium.

7. The method of claim 4, wherein said heart valve is cultured in vitro for a period of between 48 hours and 5 days.

8. A heart valve prepared by the method of any one of claims 4–7.

9. A method of preparing a heart valve for transplantation into a patient, comprising:
   (a) removing said heart valve from a donor animal;
   (b) culturing said heart valve in vitro in the presence of an agent that induces a reduction of major histocompatibility antigens, wherein said agent consists of serum derived from a species of animal other than that of the donor animal, for a period of time sufficient to reduce antigens inducing inflammation upon transplantation; and
   (c) either:
      (I) implanting the cultured heart valve of step (b) into said patient; or
      (ii) preserving said heart valve by freezing or chemical treatment.

10. The method of claim 9, wherein said donor animal is a pig.

11. The method of claim 9, wherein said heart valve is cultured in growth medium containing primate serum, and said primate serum constitutes between 5% and 20% by volume of the growth medium.

12. The method of claim 9, wherein said heart valve is cultured in vitro for a period of between 48 hours and 5 days.

13. A heart valve prepared by the method of any one of claims 9–12.

14. In a method of preserving a heart valve for transplantation into a patient, said method comprising surgically removing said heart valve from a donor animal and preserving it by freezing or chemical treatment, an improvement comprising: incubating said heart valve in vitro in the presence of primate serum for a period of time sufficient to reduce antigens inducing inflammation after transplantation.

15. The improvement of claim 14, wherein said donor animal is a pig.

16. The improvement of claim 14, wherein said heart valve is incubated in growth medium containing said primate serum, and said primate serum constitutes between 5% and 20% by volume of the growth medium.

17. The improvement of claim 14, wherein said heart valve is incubated in vitro for a period of between 48 hours and 5 days.

18. In a method of preserving a heart valve for transplantation into a patient, said method comprising surgically removing said heart valve from a donor animal and preserving it by freezing or chemical treatment, an improvement comprising: incubating said heart valve in vitro in the presence of an agent that induces a reduction of major histocompatibility antigens, wherein said agent consists of serum derived from a species of animal other than that of the donor animal, for a period of time sufficient to reduce antigens inducing inflammation after transplantation.

19. The improvement of claim 18, wherein said donor animal is a pig.

20. The improvement of claim 18, wherein said heart valve is incubated in growth medium containing primate serum, and said primate serum constitutes between 5% and 20% by volume of the growth medium.

21. The improvement of claim 18, wherein said heart valve is incubated in vitro for a period of between 48 hours and 5 days.

* * * * *

UNITED STATES PATENT AND TRADEMARK OFFICE
CERTIFICATE OF CORRECTION

| | | |
|---|---|---|
| PATENT NO. | : 6,592,618 B2 | Page 1 of 1 |
| APPLICATION NO. | : 09/793400 | |
| DATED | : July 15, 2003 | |
| INVENTOR(S) | : Chen et al. | |

It is certified that error appears in the above-identified patent and that said Letters Patent is hereby corrected as shown below:

In column 1, lines 11-13, of the issued patent, the paragraph after "Statement of Government Support" should be corrected to specify the source of funding. The corrected paragraph should read as follows:

-- This invention was made with Government support under Grant No. HL009966 awarded by the National Institutes of Health. The U.S. Government therefore has certain rights in the invention. --

Signed and Sealed this

Eighteenth Day of August, 2009

David J. Kappos
*Director of the United States Patent and Trademark Office*